United States Patent [19]
Schwartz et al.

[11] Patent Number: 5,374,544
[45] Date of Patent: Dec. 20, 1994

[54] MUTATED SKELETAL ACTIN PROMOTER

[75] Inventors: Robert J. Schwartz; King L. Chow, both of Houston, Tex.

[73] Assignee: Baylor College of Medicine, Houston, Tex.

[21] Appl. No.: 823,024

[22] Filed: Jan. 15, 1992

Related U.S. Application Data

[63] Continuation of Ser. No. 470,958, Jan. 26, 1990, abandoned.

[51] Int. Cl.$^5$ ............ C12N 15/00; C12N 5/00; C07H 17/00
[52] U.S. Cl. .............. 435/172.3; 435/240.2; 536/24.1
[58] Field of Search ............ 935/33, 36; 435/172.3

[56] References Cited

FOREIGN PATENT DOCUMENTS 0174608 3/1986 European Pat. Off. ...... C12N 15/00

OTHER PUBLICATIONS

Keindel (1985) Proced. Natl. Acad. Sci. 82, 488–492.
Miwa et. al. 1987 Molec & Cell Bio 7, 2803–2813.
Andersen, et al., "Metal-Dependent Binding of a Factor in Vivo to the Metal-Responsive Elements of the Metallothionein 1 Gene Promotor", *Mol. Cell. Biol.*, vol. 7, pp. 3574–3581 (1987).
Baldwin & Burden, "Muscle-Specific Gene Expression Controlled by a Regulatory Element Lacking a Myod-1-Binding Site", *Nature*, vol. 341, pp. 716–720 (1989).
Bergsma, et al., "Delineation and Characterization of Cis-Acting DNA Sequences Required for the Regulated Expression and Transcriptional Control of the Chicken Skeletal α-Actin Gene", *Mol. Cell. Biol.*, vol. 6, No. 7, pp. 2462–2475 (1986).
Carroll, et al., "A 29-Nucleotide DNA Segment Containing an Evolutionarily Conserved Motif is Required in Cis for Cell-Type-Restricted Repression of the Chicken α-Smooth Muscle Actin Gene Core Promoter", *Mol. Cell. Biol.*, vol. 8, pp. 241–250 (1988).
Chang, et al., "Isolation and Characterization of Six Different Chicken Actin Genes," *Mol. Cell. Biol.*, vol. 4, pp. 2498–2508 (1984).
Fornwald, et al., "The Complete Nucleotide Sequence of the Chick α-Actin Gene and Its Evolutionary Relationship to the Actin Gene Family," *Nucleic Acids Res.*, vol. 10, pp. 3861–3876 (1982).
Gorman, et al., "Recombinant Genomes Which Express Chloramphenicol Acetyltransferase in Mammalian Cells", *Mol. Cell. Biol.*, vol. 2, pp. 1044–1051 (1982).
Grichnik, et al., "Tissue Restricted and Stage Specific Transcription is Maintained with 411 Nucleotides Flanking the 5' End of the Chicken α-Skeletal Actin Gene," *Nucleic Acids Res.*, vol. 14, pp. 1683–1701 (1986).
Hayward and Schwartz, "Sequential Expression of Chicken Actin Genes During Myogenesis", *J. Cell. Biol.*, vol. 102, pp. 1485–1493 (1986).
Hu, et al., "The Complete Sequence of the Mouse Skeletal α-Actin Gene Reveals Several Conserved and Inverted Repeat Sequences Outside of the Protein-Coding Region", *Mol. Cell. Biol.*, vol. 6, pp. 15–25 (1986).
Jameson, et al., "Trans-Acting Factors Interact with a Cyclic AMP Response Element to Modulate Expression of the Human Gonadotropin α Gene," *Mol. Cell. Biol.*, vol. 7, pp. 3032–3040 (1987).

(List continued on next page.)

Primary Examiner—Elizabeth C. Weimar
Assistant Examiner—Deborah Crouch
Attorney, Agent, or Firm—Fulbright & Jaworski

[57] ABSTRACT

A mutated skeletal actin promoter which differs from the naturally occurring DNA sequence by nucleotide substitution has been found to increase gene expression. The mutation sites are specific to the cis-acting regions of the gene. Double mutations created a strong promoter. Transformed myogenic cells had ten times the transcriptional activity over the wild type. The mutated skeletal actin promoter can be used to overly express polypeptides, particularly in myogenic cells.

31 Claims, 6 Drawing Sheets

OTHER PUBLICATIONS

Kunkel, "Rapid and Efficient Site-Specific Mutagenesis Without Phenotypic Selection", *Proc. Nat'l. Acad. Sci. U.S.A.*, vol. 82, pp. 488–492 (1985).

Kunkel, et al., "Rapid and Efficient Site-Specific Mutagenesis Without Phenotypic Selection", *Meth. Enzymol.*, vol. 154, pp. 367–382 (1987).

Miller, "Assay of β-Galactosidase", *Experiments in Molecular Genetics, Cold Spring Harbor Laboratory*, Cold Spring Harbor, N.Y., pp. 352–355 (1972).

Minty & Kedes, "Upstream Regions of the Human Cardiac Actin Gene That Modulate Its Transcription in Muscle Cells: Presence of an Evolutionarily Conserved Repeated Motif," *Mol. Cell. Biol.*, vol. 6, pp. 2125–2136 (1986).

Norton & Coffin, "Bacterial β-Galactosidase as a Marker of Rous Sarcoma Virus Gene Expression and Replication", *Mol. Cell. Biol.*, vol. 5, pp. 281–291. (1985).

Schwartz et al., "Identification of Cis-Acting Regulatory Elements of the Chicken Skeletal α-Actin Gene Promoter", *Cellular & Molecular Biology of Muscle Development*, UCLA Symposia Series, vol. 93, pp. 653–667, Alan R. Liss, Inc. (1989).

Schwartz, et al., "Regulation of Muscle Differentiation: Cloning of Sequences from α-Actin Messenger Ribonucleic Acid", *Biochemistry*, vol. 19, pp. 5883–5890 (1980).

Schwartz & Rothblum, "Regulation of Muscle Differentiation: Isolation and Purification of Chick Actin Messenger Ribonucleic Acid and Quantification with Complementary Deoxyribonucleic Acid Probes", *Biochemistry*, vol. 19, pp. 2506–2514 (1980).

Schwartz & Rothblum, "Gene Switching in Myogenesis: Differential Expression of the Chicken Actin Multigene Family", *Biochemistry*, vol. 20, pp. 4112–4129 (1981).

Wu, "Two Protein-Binding Sites in Chromatin Implicated in the Activation of Heat-Shock Genes", *Nature*, vol. 309, pp. 229–241 (1984).

Zakut, et al., "Nucleotide-Sequence of the Rat Skeletal Muscle Actin Gene", *Nature*, vol. 298, pp. 857–859 (1982).

Zoller & Smith, "Oligonucleotide-Directed Mutagenesis of DNA Fragments Cloned into M13 Vectors", *Meth. Enzymol.*, vol. 100, pp. 468–500 (1983).

J. Geisselsoder, et al., "Efficient Site-Directed In Vitro Mutagenesis" *BioTechniques* 5:786–791 (1987).

C. Gorman, et al., "The Rous Sarcoma virus long terminal repeat is a strong promoter when introduced into a variety of eukaryotic cells by DNA-mediated transfection" *Proc. Natl. Acad. Sci*, USA 79:6777–6781 (1982).

M. Haltiner, et al., "A novel strategy for constructing clustered point mutations" *Nucleic Acids Research* 13:1015–1025 (1985).

S. McKnight, et al., "Transcriptional Control Signals of a Eukaryotic Protein-Coding Gene" *Science* 217:316–324 (1982).

R. Myers, et al., "Fine Structure Genetic Analysis of a β-Globin Promoter" *Science* 232:613–618 (1986).

R. Myers, et al., "A General Method for Saturation Mutagenesis of Cloned DNA Fragments": *Science* 229:242–247 (1985).

E. Winters, et al. "A method to detect and characterize point mutations in transcribed genes: Amplification and overexpression of the mutant c-Ki-ras allele in human tumor cells" *Proc. Natl. Acad. Sci.*, USA 82:7575–7579 (1985).

M. Zoller, et al., "Oligonucleotide-directed and mutagenesis using M13-derived vectors: an efficient and general procedure for the production of point mutations in any fragment of DNA" *Nucleic Acids Research* 10:6487–6500 (1982).

FIGURE 1

```
        -200       -190       -180       -170       -160       -150
5' - CCG GGGGGGCCCG GCAGACGCTC CTTATACGGC CCGGCCTCGC TCACCTGGGC CGCGGGCCAGG

-140       -130       -120       -110       -100       -90
    AGCGCCTTCT TTGGGCAGCG CCGGGGCCGGG GCCGCGCCGG GCCCGACACC CAAATATGGC

-80        -70        -60        -50        -40        -30
    GACGGGCCGGG GCCGCATTCC TGGGGGCCGG GCGGTGCTCC CGCCCGCCTC GATAAAGGC

-20        -10        +1
    TCCGGGGCCCG GCGGGCGGCCC ACGAGC  -3'
```

FIGURE 2

```
              -110       -100        -90        -80        -70        -60
               .          .          .          .          .          .
MCAT        GGGCCGCGCCGGGCCCGACACCCAAATATGGCGACGGCCGGGGCCGCATTCCTG

M18CAT      ------A-ATCT-----------------------------------------

M17CAT      ------------AGATCT-----------------------------------

M16CAT      ------------------AGAT-T-----------------------------

M15CAT      -------------------------GATCT-----------------------

M14CAT      -------------------------------AGAT-T----------------

M13CAT      -------------------------------------AGATCT----------

M12CAT      -------------------------------------------AGAT-T----
```

FIGURE 3

|        | -150 | -140 | -130 | -120 | -110 |
|--------|------|------|------|------|------|
| MCAT   | ACCTGGGCCGCGGCCAGGAGCGCCTTCTTTGGGCAGCGCCGGGCCGGGGCCGCGCCGG |
| M26CAT | ----A-AT-T------------------------------------------------ |
| M24CAT | ----------------A--T-T------------------------------------ |
| M23CAT | ----------------------AGA--------------------------------- |
| M22CAT | --------------------------AGATCT-------------------------- |
| M21CAT | ------------------------------------AT-T------------------ |
| M20CAT | -----------------------------------------A-AT-T----------- |
| M19CAT | -----------------------------------------------A-AT-T----- |

MUTATED SKELETAL ACTIN PROMOTER

ORIGIN OF THE INVENTION

The invention described herein was made using federal funds and may be manufactured or used by or for the government of the United States of America for governmental purposes without payment of any royalties thereon or therefor.

This application is a continuation of co-pending application Ser. No. 470,958, filed Jan. 26, 1990, now abandoned.

FIELD OF THE INVENTION

The present invention relates to a mutated chicken skeletal α-actin gene promoter and its use in expressing desired polypeptides particularly in myogenic cells.

BACKGROUND OF THE INVENTION

Actin, a contractile protein, is represented by multi-gene families in warm blooded vertebrate genomes. Actin is expressed in myogenic tissues such as skeletal, cardiac and smooth muscle. Some very low level expression of actin has been noted in non-myogenic tissue. The α-skeletal actin gene is a single copy gene, highly conserved during vertebrate evolution, and is expressed exclusively at high levels in adult skeletal muscle. The skeletal α-actin gene has been characterized in chicken (Fornwald et al., *Nucleic Acids Res.*, Vol. 10, pp.3861–3876 (1982)), rat (Zak et al., *Nature*, Vol. 298, pp.857–859 (1982)), mouse (Hu et al., *Mol. Cell. Biol.*, Vol. 6, pp.15–25 (1986)) and human (Minty and Kedes, *Mol. Cell. Biol.*, Vol. 6, pp.2125–2136 (1986)) genomes at the level of nucleic acid sequencing.

Genes that have been characterized and sequenced such as the chicken skeletal α-actin gene can be mapped to determine the region of the gene that is not expressed and the region of the gene that is expressed to code the α-actin protein. Parts of the unexpressed portion of the gene determines gene expression, that is when and how the expressed gene is copied in the cell. Part of the process includes mRNA transcription which is necessary for gene expression.

Usually specific regulatory sequences or elements are embedded adjacent to or within protein coding regions of DNA. These elements, located adjacent to the gene, are termed cis-acting elements. These signals are recognized by other diffusable biomolecules in trans to potentiate the transcriptional activity. These biomolecules are termed trans-acting factors. The presence of trans-acting factors and cis-acting sequences, and their appropriate association has been shown to determine the expression activity of a gene.

Cis-acting elements can be further divided into three parts, the proximal promoter, the distal promoter and the enhancer/silencer sequences. The proximal promoter usually refers to a DNA fragment of about 50 bp to 100 bp in the 5'-flanking DNA upstream of the cap site or the RNA transcriptional initiation site. The proximal promoter can drive transcription at a basal level activity. The distal promoter is a sequence further 5' to the proximal promoter. Its major function is to modulate the transcriptional activity in a specific pattern, e.g., metal induction (Anderson et al., *Mol. Cell. Biol.*, Vol. 7, pp.3579–3581 (1987)), heat shock induction (e.g. Wu, *Nature*, Vol. 309, pp.229–241 (1984)) or cAMP induction (Jameson et al., *Mol. Cell. Biol.*, Vol 7, pp.3032–3040 (1987)). The enhancer or silencer is a sequence, which can be located at any distance from the gene, and function to increase or decrease the gene expression in an orientation-independent manner. The initiation of transcription is then determined by the factors recognizing these sequences. The enhancer binding factors and the distal promoter binding factors may interact with each other and influence the events at the proximal promoter by either promoting the formation of a transcription complex or enhancing the initiation of the RNA polymerase II on the DNA template.

Some gene expression such as α-actin is tissue specific such that the levels of the protein expressed is different in myogenic and non-myogenic tissue. Transient transfection experiments demonstrated that 411 nucleotides of DNA flanking the 5' end of the skeletal α-actin gene appeared to be responsible for its tissue restricted (not inducible in primary brain cell cultures, and COS-7) and developmentally appropriate transcription of the bacterial reporter gene chloramphenicol acetyltransferase (CAT) in chicken primary myoblasts. Grichnik et al., "Tissue restricted and stage specific transcription is maintained with 411 nucleotide flanking 5' end of the chicken α-skeletal actin gene.", *Nucleic Acids Res.*, Vol. 14, pp. 1683–1701 (1986). It was also shown by S1mapping that the fusion gene CAT mRNA transcripts are under the transcriptional control of the α-actin 5'-flanking region and are accurately initiated at a surrogate start site 32 bp upstream of the CAT AUG translation initiation site.

The cis-acting regions of the chicken skeletal α-actin gene have been examined and located to some extent in the 5'-flanking region. Transgenic mice with the integrated skeletal α-actin promoter with the cis-acting regions showed preferential expression of the CAT gene in myogenic tissue. Schwartz et al., "Identification of Cis-Acting Regulatory Elements of the Chicken Skeletal α-Actin Gene Promoter," *Cellular and Molecular Biology of Muscle Development*, pp. 653–667, Alan R. Liss, Inc. (1989) and Bergsma et al., "Delimitation and Characterization of cis-acting DNA sequences Required for the Regulated Expression and Transcriptional Control of the Chicken α-Actin Gene," *Molecular and Cellular Biology*, Vol. 6, No. 7, pp. 2462–2475 (July 1986). Both of the foregoing articles are incorporated by reference herein.

The promoter was determined to have a 202 base pair 5'-flanking region which includes several cis-acting elements. The first regulatory site 5' to the cap site is the ATAAAA box between −29 bp and −24 bp which appears to be analogous to the TATA box which is involved with accurate initiation of most RNA polymerase II transcribed genes. Mutations of the gene made by nucleotide substitutions were used to identify the proximal promoter and distal promoter. The proximal promoter also termed the downstream promoter, is −94 bp to −74 bp 5' to the cap site and a CCAAT Box Associated Repeats (CBARs). Similar CBAR sequences have been found in many muscle-specific genes. The distal promoter is an upstream CBAR between −138 bp and −123 bp.

Mutations in the downstream CBAR regions caused complete inhibition of the promoter region in myogenic and non-myogenic cells. Mutation in the upstream CBAR reduced levels to 5% or less in myogenic cells. (Schwartz et al. 1989). Most of the mutations studied were in the cis-acting regions. One mutation at −154 bp to −149 bp increased tissue expression three-fold in non-myogenic tissue (fibroblasts) was more than 10 base pairs from the upstream CBAR. None of the mutated promoter regions contained nucleotide substitutions in more than one site.

SUMMARY OF THE INVENTION

The present invention is a mutation scheme for the promoter region from the 5'-flanking DNA of the chicken skeletal α-actin gene. The mutations are at least three nucleotide substitutions from the naturally occurring gene in a six consecutive DNA sequence within the 10 base pairs (base pair sometimes abbreviated as bp) adjacent to and including one base pair of the positive cis-acting sites. The region of mutation includes one base pair on either end of the cis-acting sites and the adjacent 10 base pairs. The mutated promoter region can be linked to a DNA sequence coding for a polypeptide desired to be expressed. The polypeptide can be any polypeptide desired for expression including but not limited to known proteins. Although the promoter can be linked directly to the DNA sequence coding for the polypeptide to be expressed, constructs may be made with other DNA sequences as desired such as signal sequences to aid in secretion or sequences to provide translational stability for the expressed polypeptide. The mutated skeletal actin promoter may be useful in combination with other known enhancers, promoters or the like.

The 5'-flanking region is at least 202 bp from the mRNA cap site of the chicken skeletal α-actin gene. The numbering of base pairs starts with the cap site as +1 and the promoter region is at least −202 bp from the cap site. In this region, there are four positive regulatory sites or cis-acting sites −191 bp to −174 bp; −138 bp to −123 bp; −94 bp to −78 bp; and −29 bp to −24 bp. The nucleotide substitutions of as few as three or as great as six which mutate the promoter cause increased expression of a protein associated with the mutated promoter. The mutated skeletal actin promoter, particularly those with two mutated sites, have greatly increased protein expression over the unsubstituted wild type. Some of the double mutations have been shown to express a marker gene about twenty times more active than the SV40 early promoter and 72 bp enhancer, a strong known promoter.

The mutated skeletal actin promoter is used in preparing DNA constructs as discussed above. These constructs are incorporated into transfection vectors known in the art. These vectors containing the construct are cultured with myogenic cells which are transformed to include the DNA construct including the mutated skeletal actin promoter. The myogenic cell types include heart, skeletal and smooth muscle cells. The mutated skeletal actin promoter produces increased amounts of the selected polypeptide or protein in myogenic cells. Since the skeletal actin promoter has higher levels of protein expression in myogenic tissue rather than non-myogenic tissue, and the mutated promoter has been shown to increase production in both systems; myogenic cells are chosen for protein production for this invention because of the increased levels of protein obtained.

The transfected myogenic cell cultures of this invention contain the mutated skeletal actin promoter in a construct with the DNA sequence of the polypeptide desired to be over expressed. The overly expressed protein may be harvested and purified as desired. The mutated skeletal actin promoter drives the expression of the desired polypeptide.

DETAILED DESCRIPTION OF THE INVENTION

The chicken skeletal α-actin gene was isolated from the chicken genomic DNA. The 25 kb Eco RI fragment of chicken genomic DNA, isolated from a λ Charon 4A vector, contains the 6.2 kb skeletal α-actin gene on a single Hind III fragment which was reductively subcloned into the Hind III site of pBR322. Chang et al., *Mol. Cell. Biol.*, Vol. 4, pp. 2498–2508 (1984). Portions of the skeletal α-actin gene containing 2 kb of the 5'-flanking sequence and promoter region released by Hind III/Nae I complete digestion and a 2.3 kb fragment containing 5 ' flanking sequences, promoter, 5' leader and first intron plus 33 amino acids of coding was released by Hind III and a partial Nae I digest. A fragment was released by Pvu II to Nae I and contains sequences from −422 bp to −11 bp. These fragments were Hind III linked and cloned 5' to the chloramphenicol acetyltransferase (CAT) gene in the Hind III site of pSVoCAT of Gorman et al. *Mol. Cell. Biol.*, Vol. 2, pp. 1044–1051 (1982). The CAT gene expression was used as a reporter gene to measure promoter activity. The p2.OSKCAT contains a 2 kb DNA fragment of the 5' flanking region of skeletal α-actin extending from −2 kb to −11 kb, p2.3SKCAT extend from −2 kb to +312 bp and p422SKCAT extends from +422 to −11 bp as shown in Grichnik et al. *Nucl. Acids Res.*, Vol. 14, pp. 1683–1701 (1986).

A fragment of about 450 bp in length from −421 bp (Pvu II) to +24 bp (Aha II) of the α-actin gene was released by a Pvu II/Aha II double digestion of p2.3 KbSKCAT. The sticky ends were filled in by Klenow and then ligated to Hind III linkers. The linked fragment was inserted into the Hind III site of the phagemid pTZ19R vector (Pharmacia, Inc.). This wild type construction, designated pTZ-MB, which contains 453 bp insert, in its single stranded DNA form was the target of site directed mutagenesis by synthetic oligonucleotides. Wild type and promoter mutants were subcloned next to the Tn9CAT gene in the vector pT20CAT.

Site directed mutagenesis was based on the methodology proposed by Zoller and Smith (*Meth. Enzymol.* Vol. 100, pp. 468–500 (1983)), and Kunkel's selection protocol (*Proc. Natl. Acad. Sci. USA*, Vol. 82, pp.488–492 (1985)); (*Meth. Enzymol.*, Vol. 154, pp. 367–382 (1987)) with the following modifications. Other site directed mutagenesis procedures known in the art can be used to practice this invention. The ssDNA for in vitro manipulation was prepared by the *E. coli* BW313 which was deficient in dUTPase (dut⁻⁻ resulting high concentration of intracellular dUTP) and uracil N-glycosylase (ung⁻resulting disability in removing misincorporated uracils). The bacterial host *E. coli* BW3123 transformed with pTZ-MB was grown to a concentration of $10^7$ per ml and infected with helper phage M13K07 at an infection multiplicity of 10. After incubation, bacteria was removed by centrigufation and the uridine containing single stranded pTZ-MB DNA was isolated by polyethylene glycol precipitation. One ug of the ssDNA was mixed with approximately 30 ng of mutant 30-mer oligonucleotide which was synthesized to have 12 bp complementary sequence on both sides surrounding 6 bp of Bgl II recognition sequence in the middle.

In order to assess any cell-type specificity within the 5' promoter region of the skeletal α-actin gene, transfectable cell types were selected which exhibited very high and very low relative levels of expression of the endogenous α-actin gene. Chick embryo myoblast cultures were selected as the preferred positive expression system as described in Hayward and Schwartz, *J. Cell. Biol.*, Vol. 102, pp.1482-1493 (1986) which is incorporated by reference into this disclosure. Passaged chick embyro fibroblasts were chosen as the negative expression system since they have been shown to accumulate only 5% or less of the amount of skeletal α-actin transcripts detected in cultured myotubes. Carroll et al., *Mol. Cell. Biol.*, Vol. 8, pp. 241-250 (1988). Bgl II linked scanning promoter mutants and wild type cloned into promoterless plasmid vectors containing the chloramphenicol acetyltransferase gene (CAT) were cotransfected with plasmids containing the RSV-β-galactosidase gene into primary myoblast and fibroblast cultures. Also, a CAT construct with no promoter (oCAT) was used as a control. The results of CAT assays were standardized with the β-galactosidase (GAL) assays. The wild type construction had previously been shown to have at least a 75 fold greater transcriptional activity in myotubes than in fibroblasts, demonstrating cell type restricted expression. Schwartz et al. (1989).

Figure 1:
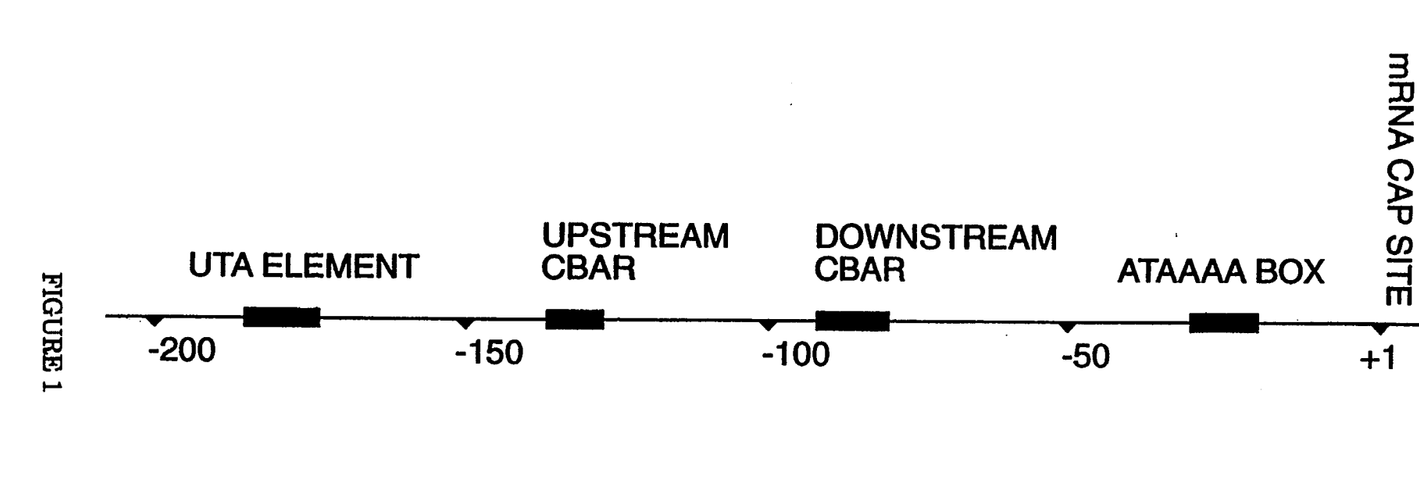
FIG. 1 is a schematic of the promoter region of the chicken skeletal α-actin gene indicating cis-acting sites.
Figure 2:
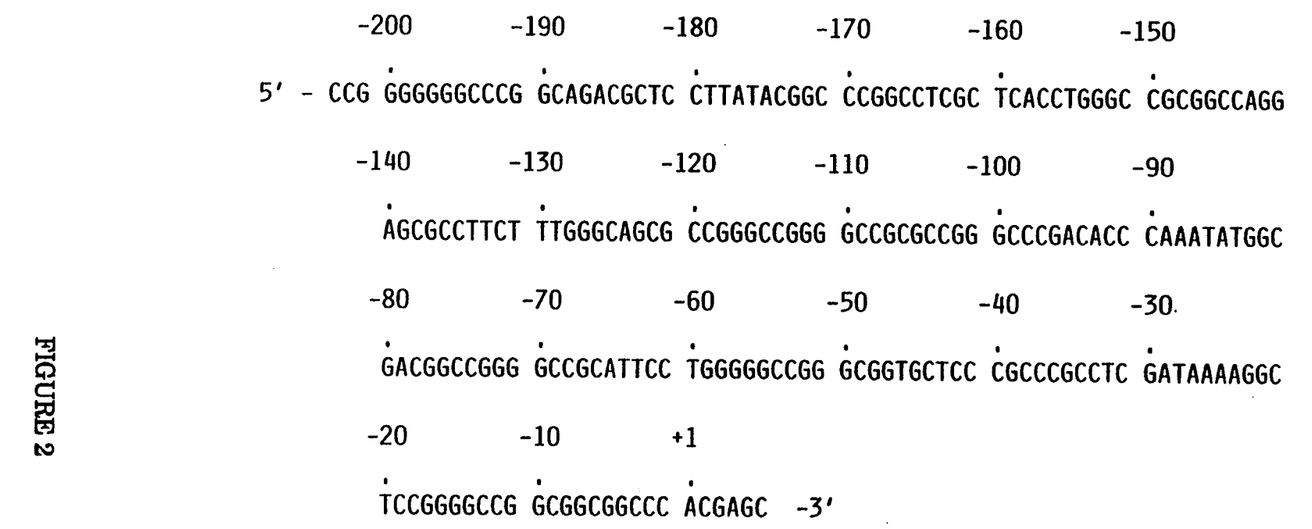
FIG. 2 is the naturally occurring DNA sequence for the chicken α-actin skeletal promoter which includes the cis-acting sites.

FIG. 1 is a schematic showing the cis-acting sites of the chicken skeletal α-actin promoter gene. The +1 indicates the mRNA cap site. The ATAAAA box, downstream CBAR and upstream CBAR are shown as well as an upstream TA rich region indicated by UTA element. FIG. 2 is a detail of the DNA nucleotide sequence corresponding to the schematic of FIG. 1. In both figures the +1 base pair is the mRNA cap site.

The mutated skeletal actin promoters of this invention include at least three and up to six nucleotide substitutions from the DNA sequence shown in FIG. 2 in 11 consecutive base pairs starting with the base pair on either end of the cis-acting sites. Up to six nucleotides may be substituted. The substitutions occur within a consecutive six nucleotide site.

The following examples illustrate the use of the mutation scheme with myogenic and non-myogenic tissue expression cultures. The transfection and enzymatic assays are described below.

Primary myoblast cultures were established by mechanically dissociating tissue from the breasts of 11-day-old chicken embryos as described in Hayward and Schwartz (1986). The myoblast-enriched cell populations were seeded into collagen-coated 100-mm-diameter dishes at a density of $2.0 \times 10^6$ to $2.5 \times 10^6$ cells per plate in minimal essential medium supplemented with 10% horse serum, 5% chicken embryo extract, and gentamicin sulfate (50 ug/ml). After 24 h, the medium was changed to 10% horse serum, 2% chicken embryo extract, and gentamicin sulfate (50 ug/ml). Primary cultures of chicken embryo fibroblasts were established by trypsinizing 96-h primary myotube cultures and passaged every two to three days. All experiments were performed with fibroblasts between passages 3 and 5.

Fibroblasts were seeded into 100-mm-diameter culture dishes 24 h before transfection at a density of $2.0 \times 10^6$ to $2.5 \times 10^6$ cells per plate in medium of 10% horse serum-2% chicken embryo extract-gentamicin sulfate (50 ug/ml). Cultures were incubated in 5% $CO_2$ at 37° C. At 24 h after plating, primary cultures were transfected with a total of 6 ug of the hybrid CAT vector construct DNA plus 2.0 ug of pRSVGAL per 100-mm-diameter dish in calcium phosphate precipitates.

For competition study, 3 ug of M-CAT was used with 1.5 ug of pRSVGAL. Competitor DNA was added according to the molar ratio of the competing fragment to the cells, which were harvested by scraping 72 h posttransfection and assayed for CAT activity as described in Gorman et al., *Mol. Cell. Biol.*, Vol. 2, pp.1044-1051 (1982), which is incorporated by referenced in this disclosure. To control for variations in both cell numbers and transfection efficiency, all recombinant and control clones were cotransfected with the same amount of pRSVGAL, a eucaryotic expression vector in which the *E. coli* β-galactosidase (lacZ) structural gene is under the transcriptional control of the Rous sarcoma virus long terminal repeat. Lysates prepared from the harvested cells were assayed for both CAT activity, which was used as a measure of promoter efficiency, and β-galactosidase activity, which was used as an internal standard to normalize the CAT activity directed by the test plasmid.

Assays of β-galactosidase activity under the conditions described by Miller, "Experiments in molecular genetics, Cold Spring Harbor Laboratory," pp.352-355, Cold Spring Harbor, N.Y. (1972), and Norton and Coffin, "Bacterial β-galactosidase as a marker of Rous sarcoma virus gene expression and replications," *Mol. Cell. Biol.*, Vol. 5, pp.281-291 (1985), were performed with 5 ul of cell extract, which was added to a solution of 50 ul of 3.36M 2-mercaptoethanol, 50 ul of 30 mM $MgCl$, and 650 ul of o.1M $Na_2HPO_4$ adjusted to pH 7.3 at 37° C. with 0.1M $NaH_2PO_4$. The reaction was started by the addition of 750 ul of 4.38 mM o-nitrophenyl-β-D-galactopyranoside (ONPG; Sigma Chemical Co.) dissolved in the sodium phosphate buffer and incubated at 37° C. for 30 to 45 min. The reaction was stopped by the addition of 500 ul of 1M $Na_2CO^3$, and $A_{410}$ was then recorded. Units were determined by the method of Miller. Transfection experiments were performed in triplicate with two independently isolated sets of chimera and control vectors, and the results were averaged. The range of individual sample values averaged 10% of the normalized value. Data are expressed as the nanomoles of acetylated [$^{14}C$] chloramphenicol per hour per microgram of CAT vector DNA transfected per unit of galactosidase activity.

EXAMPLE 1

Figure 3:
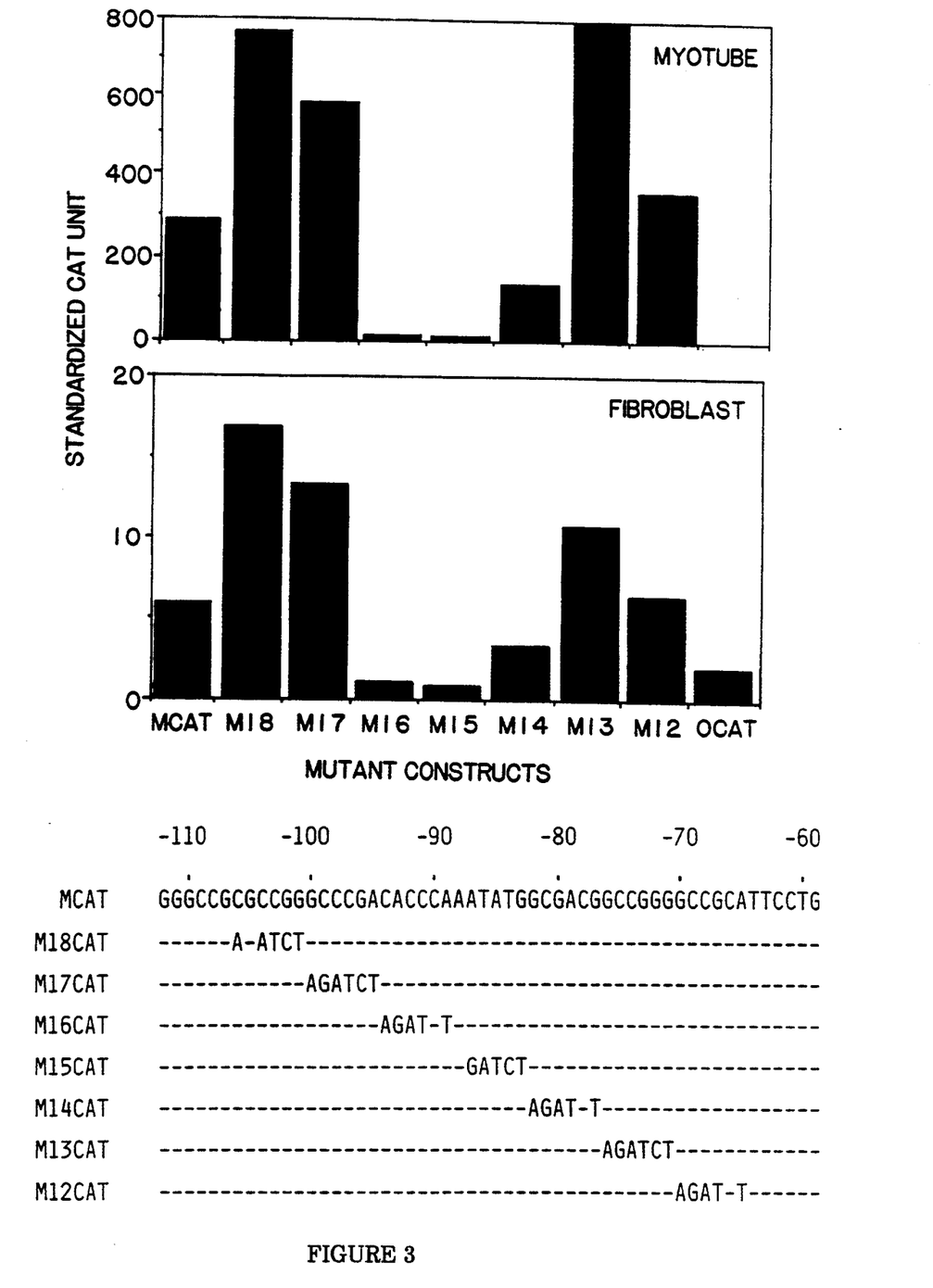
FIG. 3 illustrates the mutations of the downstream CBAR and the effects on myogenic (myotube) and non-myogenic (fibroblast) expression.

FIG. 3 shows the mutation scheme and its affects on gene expression in myogenic Cells, myotubes and non-myogenic cells, fibroblasts. The DNA sequence including the downstream CBAR −93 bp to −78 bp is designated as MCAT. The standardized CAT units are shown as measured in both myotube and fibroblast cell culture promoter sequence and CAT gene (MCAT), the CAT gene with no promoter sequence (oCAT) and the mutants. Mutants M13, M17 and M18 are five to six nucleotide substitutions from the naturally occurring promoter region and are adjacent to the downstream CBAR. M13 and M18 more than double the MCAT activity while M17 almost doubles the MCAT activity in myotubes. M13, M17 and M18 show increases in CAT activity in fibroblasts.

Alternatively, the mutations which cover the downstream CBAR, M15 and M16, caused inhibition of CAT activity. M14 which partially covers the CBAR shows a decrease in CAT activity. While M12 which is within ten nucleotides of the CBAR shows an increase in activity.

EXAMPLE 2

Figure 4:
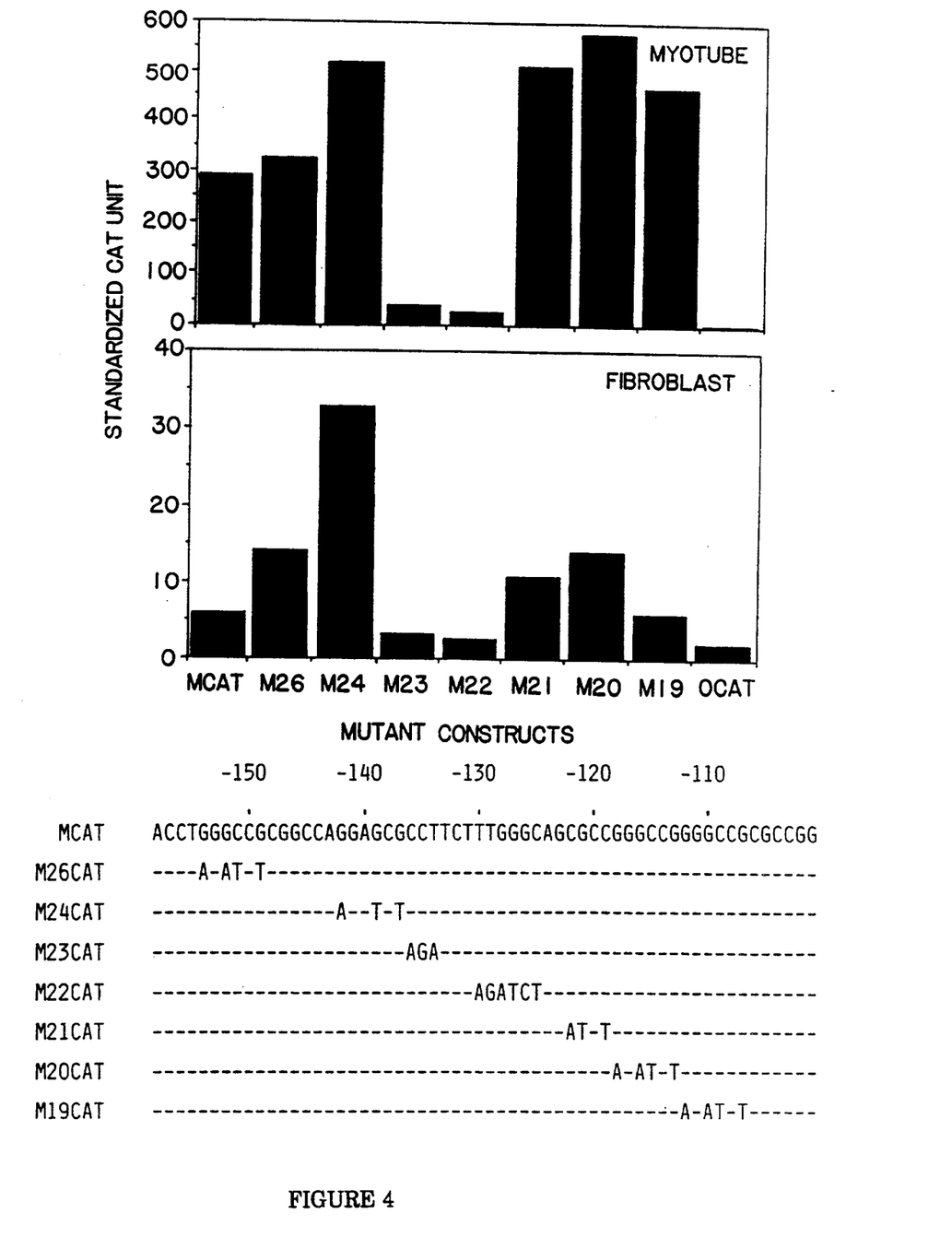
FIG. 4 illustrates the mutations of the upstream CBAR and the effects on myogenic (myotube) and non-myogenic (fibroblast) expression.

FIG. 4 shows the mutation scheme and its affects on gene expression for the upstream CBAR in the same manner as FIG. 3.

The upstream CBAR is $-138$ bp to $-123$ bp. Mutation M24, M21 and M20 are three to five nucleotide substitutions within six consecutive base pairs, and in regions adjacent to or including one base pair of the upstream CBAR. All three show increases in CAT activity in fibroblast and myotube cells. M22 and M23 which cover the upstream CBAR inhibit CAT activity.

M26 shows a slight increase in myotube and almost doubles the low expression in fibroblast. M19 on the other hand slightly lowers fibroblast and increases myotube expression. M19 and M26 are outside the ten nucleotide adjacent region of the upstream CBAR.

EXAMPLE 3

Figure 5:
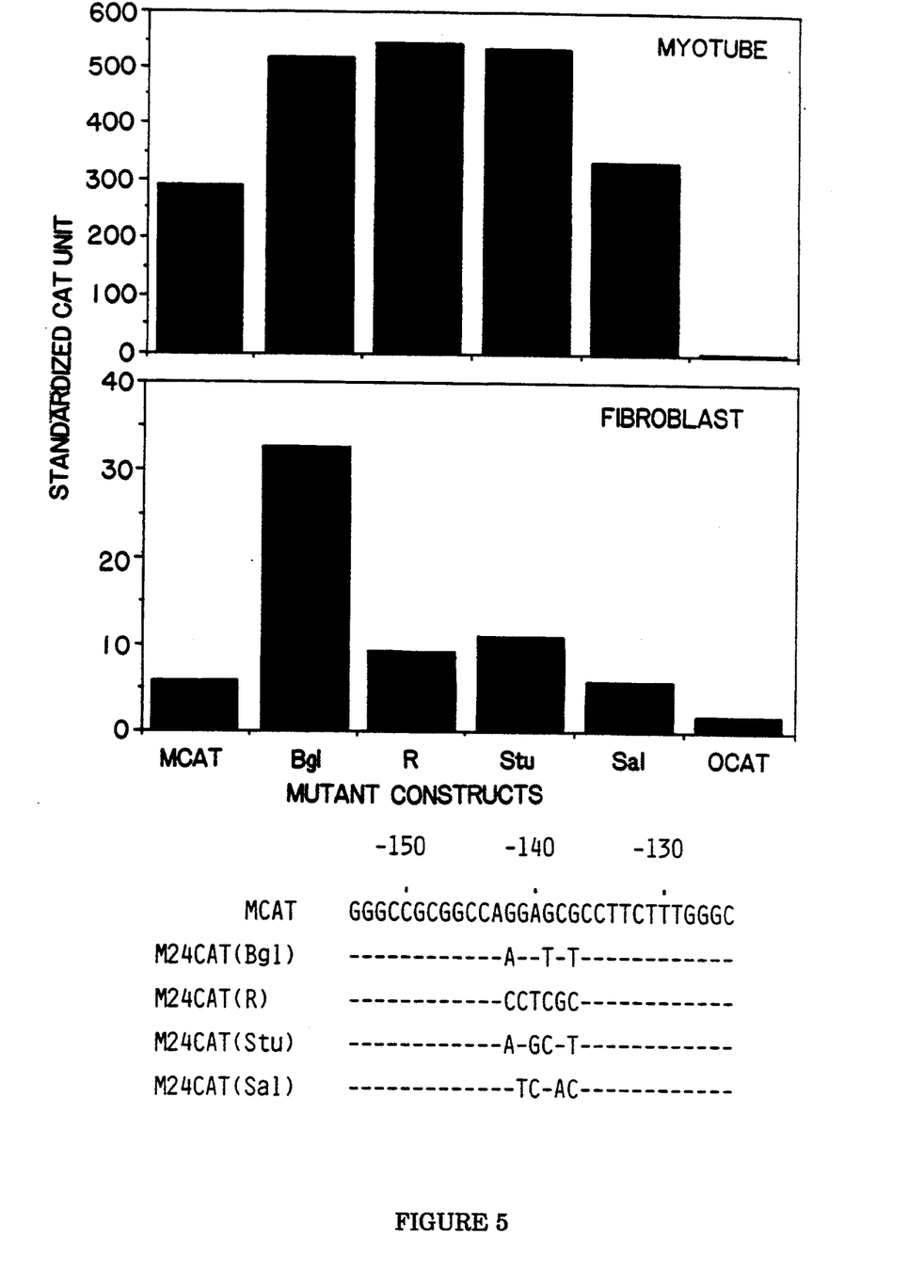
FIG. 5 illustrates multiple mutations in one consecutive six nucleotide sequence.

FIG. 5 shows multiple mutations by various nucleotide substitution in the $-142$ bp to $-137$ bp range adjacent to the upstream CBAR. The M24 CAT from Example 2 is shown as M24 CAT (Bgl). Other nucleotide substitutions were made using different mutation processes. Of the various mutations, the M24 CAT(R) and M24 CAT(Stu) showed significant increases in activity in myotubes even greater than M24 CAT (Bgl). M24 CAT(Sal) showed an increase over the wild type in myotubes. M24 CAT(R), M24 CAT(Stu) and M24 CAT(Sal) did not show the great increase in the low expression non-myogenic fibroblast system. However, the expression system of myogenic tissue is of considerable importance since the myogenic system produces far greater quantities of the polypeptide. Example 3 also shows the ability to construct mutants within the regions defined to determine the best over expression system. Those skilled in the art can perform the multiple nucleotide substitution as illustrated in Example 3.

EXAMPLE 4

Figure 6:
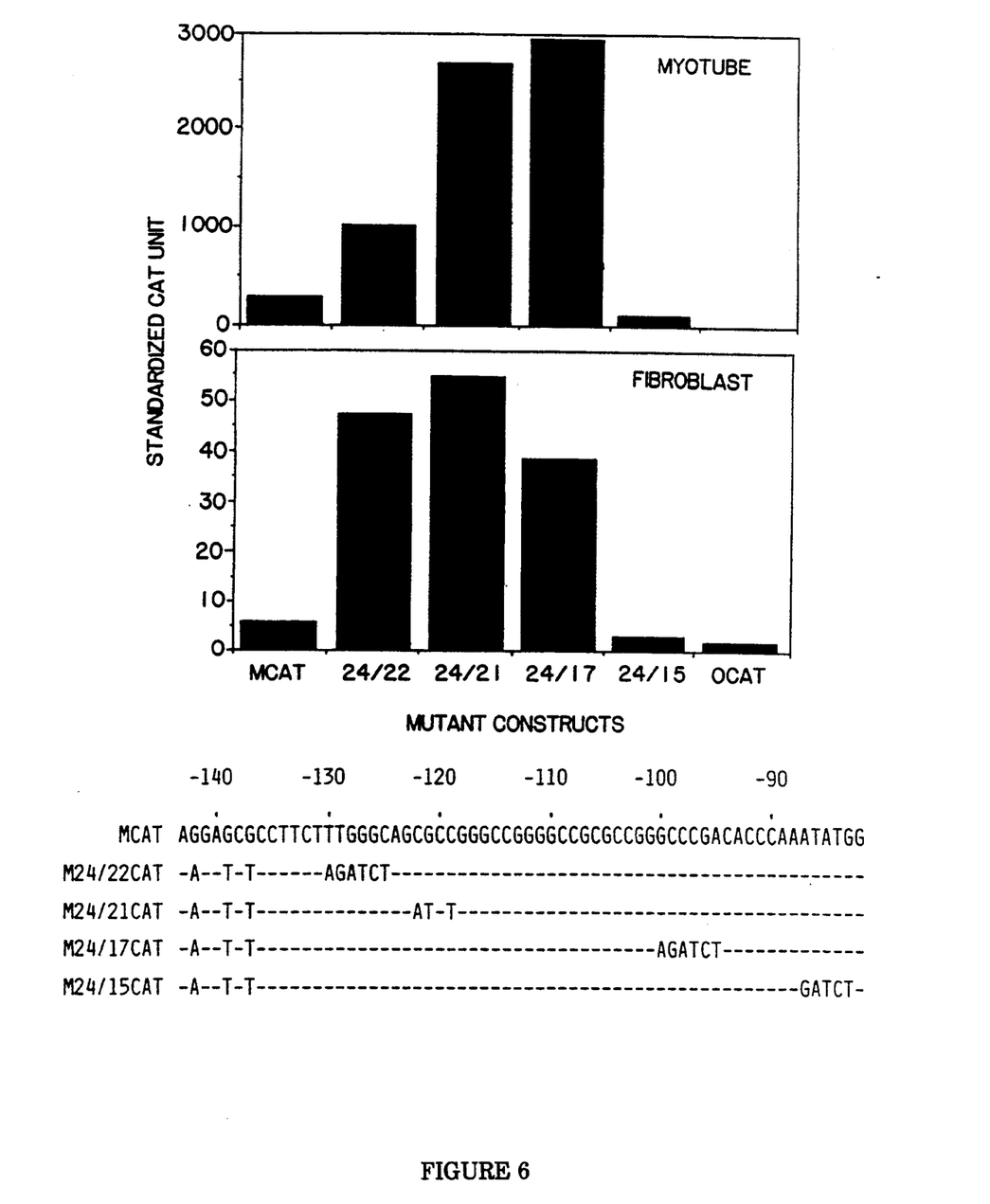
FIG. 6 illustrates the increased activity of the double site mutations.

The most dramatic increases in activity have been shown when there are two mutated sites. Double mutations were generated by preparing uridine-containing single-stranded DNA from the mutant pTZ-M24. FIG. 6 shows the wild type DNA (MCAT) with the double mutations in the corresponding DNA sequence below. Double mutation M24/22CAT and M24/21CAT shows nucleotide substitution in two sites on the upstream CBAR. The M24/17CAT combined nucleotide substitutions in sites adjacent to the upstream and the downstream CBARs. The affect of the mutation in myogenic and non-myogenic tissue is dramatic as shown in the bar graphs of FIG. 6. The M24/17CAT stimulated transcriptional activity by a factor of ten over the wild type myotube cells. M24/17CAT is approximately 20 times more active than the SV40 early promoter and 72 bp enhancer which is one of the strongest promoter/enhancer combinations known. The M24/15CAT construct combines a mutation in the adjacent to the positive cis-acting site of the upstream CBAR and a mutation covering the cis-acting downstream CBAR which is not in the mutational site of this invention. The activity in the myogenic and non-myogenic material was less than the wild type.

We claim:

1. A DNA sequence comprising:
   a promoter region from the 5'-flanking DNA of the chicken α-actin gene and including a positive cis-acting site;
   at least one mutated site in said promoter, wherein said mutated site includes at least three nucleotide substitutions in the naturally occurring DNA sequence and said mutated site promotes the overexpression of a polypeptide functionally linked to said promoter; and
   said at least one mutated site occurring in a sequence of ten consecutive base pairs adjacent to and including one base pair of said positive cis-acting site wherein said mutation results in formation of a Bgl II restriction enzyme site.

2. A DNA sequence of claim 1 wherein said promoter region is at least 202 base pairs in the 5'-flanking DNA from the cap site of the chicken skeletal α-actin gene.

3. A DNA sequence of claim 1 wherein said mutations are of no more than six nucleotide substitutions from the naturally occurring DNA sequence.

4. A DNA sequence of claim 1 wherein said nucleotide substitution is in the region of $-142$ bp and $-137$ bp in the 5'-flanking DNA from the cap site of the chicken skeletal α-actin gene.

5. A DNA sequence of claim 1 wherein said nucleotide substitution is in the region of $-100$ bp and $-94$ bp in the 5'-flanking DNA from the cap site of the chicken skeletal α-actin gene.

6. A DNA sequence of claim 1 wherein said nucleotide substitution is in the region of $-124$ bp and $-119$ bp in the 5'-flanking DNA from the cap site of the chicken skeletal α-actin gene.

7. A DNA sequence of claim 1 wherein said nucleotide substitutions is in the region of $-106$ bp and $-101$ bp in the 5'-flanking DNA from the cap site of the chicken skeletal α-actin gene.

8. A DNA sequence of claim 1 wherein said nucleotide substitutions is in the region of $-76$ bp and $-71$ bp in the 5'-flanking DNA from the cap site of the chicken skeletal α-actin gene.

9. A DNA sequence of claim 1 wherein said nucleotide substitutions is in the region of $-118$ bp and $-113$ bp in the 5'-flanking DNA from the cap site of the chicken skeletal α-actin gene.

10. A method for making a DNA construct comprising the steps of:
    isolating at least a 202 base pair sequence of a promoter region from the 5'-flanking DNA of the chicken α-actin gene, wherein said sequence includes at least one positive cis-acting site;
    mutating said sequence to form a Bgl II restriction enzyme site and wherein at least three nucleotides in a six consecutive nucleotide sequence from the naturally occurring DNA sequence is mutated and said mutation occurs within a sequence of ten consecutive base pairs adjacent to and including one base pair of the positive cis-acting site; and linking the mutated sequence with a DNA sequence coding for a polypeptide desired to be expressed, wherein said mutation promotes the over-expression of said polypeptide.

11. A method for making a DNA construct of claim 10 wherein the mutating step comprises no more than six nucleotide substitutions are made from the naturally occurring DNA sequence.

12. A method for making a DNA construct of claim 10 wherein the mutating step includes a nucleotide substitution in the region of −142 bp and −137 bp in the 5′-flanking DNA from the cap site of the chicken skeletal α-actin gene.

13. A method for making a DNA construct of claim 10 wheren the mutating step includes a nucleotide substitution in the region of −100 bp and −94 bp in the 5′-flanking DNA from the cap site of the chicken skeletal α-actin gene.

14. A method for making a DNA construct of claim 10 wheren the mutating step includes a nucleotide substitution in the region of −124 bp and −119 bp in the 5′-flanking DNA from the cap site of the chicken skeletal α-actin gene.

15. A method for making a DNA construct of claim 10 wherein the mutating step includes a nucleotide substitution in the region of −106 bp and −101 bp in the 5′-flanking DNA from the cap site of the chicken skeletal α-actin gene.

16. A method for making a DNA construct of claim 10 wherein the mutating step includes a nucleotide substitution in the region of −76 bp and −71 bp in the 5′-flanking DNA from the cap site of the chicken skeletal α-actin gene.

17. A method for making a DNA construct of claim 10 wheren the mutating step includes a nucleotide substitution in the region of −118 bp and −113 bp in the 5′-flanking DNA from the cap site of the chicken skeletal α-actin gene.

18. A method of over-expressing a polypeptide in myogenic cells comprising the steps of;
constructing the DNA sequence of claim 1;
linking said DNA sequence to a DNA sequence coding for a polypeptide desired to be over-expressed;
incorporating the resultant DNA construct into a transfection vector;
transfecting myogenic cells;
culturing the transfected myogenic cells which over-express the desired polypeptide.

19. A method to express a polypeptide in myogenic cells of claim 18 wherein, in the step of constructing the DNA sequence of the promoter region, at least one mutation site is in the region of −142 bp and −137 bp in the 5′-flanking DNA from the cap site of the chicken skeletal α-actin gene.

20. A method to express a polypeptide in myogenic cells of claim 18 wherein, in the step of constructing the DNA sequence of the promoter region, at least one mutation site is in the region of −100 bp and −94 bp in the 5′-flanking DNA from the cap site of the chicken skeletal α-actin gene.

21. A method to express a polypeptide in myogenic cells of claim 18 wherein, in the step of constructing the DNA sequence of the promoter region, at least one mutation site is in the region of −124 bp and −119 bp in the 5′-flanking DNA from the cap site of the chicken skeletal α-actin gene.

22. A method to express a polypeptide in myogenic cells of claim 18 wherein, in the step of constructing the DNA sequence of the promoter region, at least one mutation site is in the region of −106 bp and −101 bp in the 5′-flanking DNA from the cap site of the chicken skeletal α-actin gene.

23. A method to express a polypeptide in myogenic cells of claim 18 wherein, in the step of constructing the DNA sequence of the promoter region, at least one mutation site is in the region of −76 bp and −71 bp in the 5′-flanking DNA from the cap site of the chicken skeletal α-actin gene.

24. A method to express a polypeptide in myogenic cells of claim 18 wherein, in the step of constructing the DNA sequence of the promoter region, at least one mutation site is in the region of −118 bp and −113 bp in the 5′-flanking DNA from the cap site of the chicken skeletal α-actin gene.

25. A DNA sequence comprising:
a promoter region from the 5′-flanking DNA of the chicken α-actin gene and including a positive cis-acting site;
a mutation in said promoter, wherein said mutation promotes the over-expression of a polypeptide functionally linked to said promoter; and
wherein said mutation results in formation of a Stu restriction enzyme site at location −142 to −137 in FIG. 2.

26. A method for making a DNA construct comprising the steps of:
isolating at least a 202 base pair sequence of a promoter region from the 5′-flanking DNA of the chicken α-actin gene, wherein said sequence includes at least one positive cis-acting site;
mutating said sequence to form a Stu restriction enzyme site at location −142 to −137 in FIG. 2; and
linking the mutated sequence with a DNA sequence coding for a polypeptide desired to be expressed, wherein said mutation promotes the over-expression of said polypeptide.

27. A method of over-expressing a polypeptide in myogenic cells comprising the steps of;
constructing the DNA sequence of claim 25;
linking said DNA sequence to a DNA sequence coding for a polypeptide desired to be over-expressed;
incorporating the resultant DNA construct into a transfection vector;
transfecting myogenic cells;
culturing the transfected myogenic cells which over-express the desired polypeptide.

28. A DNA sequence comprising:
a promoter region from the 5′-flanking DNA of the chicken α-actin gene and including a positive cis-acting site;
a mutation in said promoter, wherein said mutation promotes the over-expression of a polypeptide functionally linked to said promoter; and
wherein said mutation is CCTCGC at location −142 to −137 in FIG. 2.

29. A method for making a DNA construct comprising the steps of:
isolating at least a 202 base pair sequence of a promoter region from the 5′-flanking DNA of the chicken α-actin gene, wherein said sequence includes at least one positive cis-acting site;

mutating said sequence to CCTCGC at location −142 to −137 in FIG. 2; and linking the mutated sequence with a DNA sequence coding for a polypeptide desired to be expressed, wherein said mutation promotes the over-expression of said polypeptide.

30. A method of over-expressing a polypeptide in myogenic cells comprising the steps of;

constructing the DNA sequence of claim 28;

linking said DNA sequence to a DNA sequence coding for a polypeptide desired to be over-expressed;

incorporating the resultant DNA construct into a transfection vector;

transfecting myogenic cells;

culturing the transfected myogenic cells which over-express the desired polypeptide.

31. A transformed myogenic cell culture comprising said cell transformed by the method of claim 18, 27 and 30.

* * * * *